United States Patent [19]

Aniuk et al.

[11] Patent Number: 4,883,699
[45] Date of Patent: Nov. 28, 1989

[54] POLYMERIC ARTICLE HAVING HIGH TENSILE ENERGY TO BREAK WHEN HYDRATED

[75] Inventors: Lawrence M. Aniuk, Santa Clara; Ronald L. Dieck, Irving; Dwayne Hardy, San Mateo, all of Calif.

[73] Assignee: Menlo Care, Inc., Palo Alto, Calif.

[21] Appl. No.: 8,117

[22] Filed: Jan. 23, 1987

Related U.S. Application Data

[63] Continuation of Ser. No. 780,543, Sep. 26, 1985, abandoned, which is a continuation-in-part of Ser. No. 653,390, Sep. 21, 1984, abandoned.

[51] Int. Cl.$^4$ .............................................. B27N 5/02
[52] U.S. Cl. ................................... 428/36.9; 525/57; 525/58; 525/123; 525/409; 525/453; 525/937; 604/264
[58] Field of Search ...................... 523/113, 115, 106; 525/57, 409, 453, 937; 428/36.9

[56] References Cited

U.S. PATENT DOCUMENTS

| | | | |
|---|---|---|---|
| 3,544,668 | 7/1968 | Dereniuk | 264/135 |
| 3,566,874 | 3/1971 | Hopewell | 604/265 |
| 3,628,988 | 12/1971 | Stol et al. | 427/2 |
| 3,632,416 | 1/1972 | Shepherd et al. | 428/245 |
| 3,695,921 | 10/1972 | Shepherd et al. | 427/2 |
| 3,708,452 | 1/1973 | Tsubakimoto | 523/502 |
| 3,773,871 | 11/1973 | Merrill | 264/22 |
| 3,792,009 | 2/1974 | Mudde | 524/291 |
| 3,810,458 | 5/1974 | Semp | 128/1 R |
| 3,816,170 | 6/1974 | Mudde | 428/522 |
| 3,821,136 | 6/1974 | Hudgin et al. | 527/302 |
| 3,822,238 | 7/1974 | Blair et al. | 528/59 |
| 3,832,458 | 8/1974 | Merrill | 424/424 |
| 3,862,452 | 1/1975 | Wichterle et al. | 623/12 |
| 3,867,329 | 2/1975 | Halpern et al. | 210/360.1 |
| 3,879,493 | 4/1975 | Mudde | 525/127 |
| 3,928,255 | 12/1975 | Milkovich et al. | 521/134 |
| 3,929,741 | 12/1975 | Laskey | 523/106 |
| 3,930,076 | 12/1975 | Kliment | 427/353 |
| 3,953,406 | 4/1976 | Marsh, Jr. | 528/75 |
| 3,961,379 | 6/1976 | Highgate | 522/116 |
| 3,975,350 | 8/1976 | Hudgin et al. | 428/78 |
| 4,055,682 | 10/1977 | Merrill | 427/36 |
| 4,085,168 | 4/1978 | Milkovich et al. | 525/59 |
| 4,119,094 | 10/1978 | Micklus et al. | 428/425 |
| 4,123,406 | 10/1978 | Stoy et al. | 526/49 |
| 4,130,517 | 12/1978 | Lundberg et al. | 523/106 |
| 4,138,382 | 2/1979 | Polmanteer | 526/279 |
| 4,156,066 | 5/1979 | Gould | 528/73 |
| 4,172,823 | 10/1979 | Stoy et al. | 526/236 |
| 4,202,880 | 5/1980 | Fildes et al. | 424/78 |
| 4,235,988 | 11/1980 | Fildes et al. | 528/79 |
| 4,279,795 | 7/1981 | Yamashita et al. | 525/311 |
| 4,286,341 | 9/1981 | Greer et al. | 427/2 |
| 4,371,686 | 2/1983 | Yamamoto et al. | 528/76 |

(List continued on next page.)

FOREIGN PATENT DOCUMENTS

| | | |
|---|---|---|
| 137686 | 4/1985 | European Pat. Off. |
| 529087 | 1/1977 | Japan |
| 56-092936 | 7/1981 | Japan |
| 56-163128 | 12/1981 | Japan |
| 224052 | 11/1968 | U.S.S.R. |
| 1511563 | 5/1978 | United Kingdom |
| 2140444 | 11/1984 | United Kingdom |

Primary Examiner—Lewis T. Jacobs
Assistant Examiner—A. Carrillo
Attorney, Agent, or Firm—Edith A. Rice; Herbert G. Burkhard

[57] ABSTRACT

An article, suitable for use as a body implant, is made from a novel composition comprising a multiple phase polymer composition comprising:

(a) a first phase which comprises a substantially non-hydrophilic polymeric component; and (b) a second phase which comprises a hydrophilic polymeric component;

said composition (i) being capable of absorbing water to an extent that it softens with a softening ratio of at least about 2:1 and/or swells with a swelling ratio of at least about 1.3:1; and (ii) when substantially completely hydrated has an energy to break of at least about 700 N-cm/cm$^3$ and a 2.5% Secant modulus of less than about 7,000 N/cm$^2$.

30 Claims, 2 Drawing Sheets

U.S. PATENT DOCUMENTS

| | | | |
|---|---|---|---|
| 4,373,009 | 2/1983 | Winn | 428/424.2 |
| 4,404,296 | 9/1983 | Schapel | 523/105 |
| 4,423,099 | 12/1983 | Mueller et al. | 428/35 |
| 4,423,184 | 12/1983 | Kopolow et al. | 525/57 |
| 4,424,305 | 1/1984 | Gould et al. | 525/127 |
| 4,426,742 | 1/1984 | Prahl | 623/7 |
| 4,427,808 | 1/1984 | Stol et al. | 523/105 |
| 4,433,072 | 2/1984 | Pusineri et al. | 523/112 |
| 4,438,253 | 3/1984 | Casey et al. | 528/86 |
| 4,438,258 | 3/1984 | Graham | 528/271 |
| 4,439,583 | 3/1984 | Gould et al. | 525/127 |
| 4,454,309 | 6/1984 | Gould et al. | 525/28 |
| 4,478,961 | 10/1984 | Tanaka et al. | 525/111 |
| 4,517,326 | 5/1985 | Cordts et al. | 523/113 |
| 4,575,532 | 3/1986 | Schmukler et al. | 525/57 |
| 4,610,671 | 9/1986 | Luther | 546/304 |

POLYMERIC ARTICLE HAVING HIGH TENSILE ENERGY TO BREAK WHEN HYDRATED

This application is a continuation of application Ser. No. 780,543, filed 9/26/85, now abandoned, which is a continuation-in-part application of U.S. Ser. No. 653,390, filed Sept. 21, 1984, now abandoned, the disclosure of which is incorporated herein by reference.

BACKGROUND OF THE INVENTION

This patent relates to a body implant which softens and/or swells when implanted in the body, a novel composition useful in preparing said implant and a method of preparing said implant. It further relates to methods of inserting a softening and/or swelling catheter or cannula into a blood vessel of an animal.

Body implants, in particular tubular implants inserted into the body such as catheters, cannulae, endotracheal tubes or the like need to be relatively stiff for ease of insertion in the body. Commercially available cannulae, for example, are typically made of fluorinated ethylene-propylene copolymer, polytetrafluoroethylene, poly(chlorotrifluoroethylene), or the like. When such commercial cannulae or catheters of such materials are left in the body for relatively long periods of time, trauma to the surrounding tissue may result.

Various compositions which soften in contact with water are known and some have been suggested for use as body implants. The following are illustrative.

U.S. Pat. No. 3,822,238, Blair et al, discloses water absorptive polyurethane polymers prepared from resins having a low ratio of carbon to oxygen to nitrogen or having ionic quaternary ammonium or salt groups in the resin backbone and a low amount of isocyanate. It is suggested that the polymers can be used as coatings or membranes or shaped by casting or machining to make body implants. There is no suggestion as to which polymers of the many disclosed would be useful for forming body implants. Nor is there any indication of what properties polymers for use as body implants should have.

U.S. Pat. No. 3,975,350, Hodgin et al, discloses hydrophilic crosslinked polyurethane systems useful as carrier systems for slow release of medication, as coatings or for body implants, such as catheters and cannulae. Again there is no suggestion as to which polyurethane systems would be useful for body implants.

U.S. Pat. No. 4,279,795, Yamashita et al, relates to materials capable of forming a hydrogel and having improved anti-thrombogenic properties. The polymer is a graft copolymer having a hydrophilic polymer backbone, e.g. a polymethacrylate, with hydrophobic moieties, e.g. polystyrene, grafted onto it. The hydrogel is said to be self-reinforcing and capable of being shaped into a tube, film, rod, etc.

U.S. Pat. No. 4,371,686, Yamamoto et al, discloses implanting into jugular and femoral veins of animals, tubes of a polyurethane containing polyoxyethylene and polyoxypropylene blocks. The polymers are said to be highly elastic and to possess anti-thrombogenic properties.

U.S. Pat. No. 4,439,583, Gould et al, discloses a polyurethane diacrylate composition which forms a hydrogel on immersion in water. The compositions are said to have a variety of uses including use in body implants such as catheters and cannulae.

U.S. Pat. No. 4,454,309, Gould et al, discloses a composition comprising a hydrophilic polyurethane resin and a polyene selected from polyalkyl esters and polyacrylic acid esters. The compositions are said to have a variety of uses including use in body implants such as catheters and cannulae.

U.K. Pat. No. 1,511,563, Ciba-Giegy AG, relates to water-insoluble hydrophilic copolymers, preferably a methacrylate copolymer. The copolymers are primarily useful as drug delivery systems. It is disclosed that the copolymers can be fashioned into substitute blood vessels or extracorporeal shunts.

Japanese Kokai Sho 52-9087 to Nakashima et al, discloses block and or graft copolymers made of hydrophilic polymer segments and hydrophobic polymer segments and having a phase-separated microstructure with one of the segments, preferably the hydrophilic, forming a continuous phase and the other a dispersed phase. The copolymers are said to have good anti-thrombogenic properties. The copolymers are said to be useful for medical and therapeutic equipment that may come into contact with blood, such as, for example, vascular catheters, cannulae, shunts, etc.

In summary, while a great number of compositions are disclosed in each of these patents, there is no indication of which particular compositions would be suitable for use as a body implant, such as a catheter or cannula. Where a particular composition has been made into a catheter or cannula, the composition selected is one which does not provide a body implant having desired properties.

It has now been discovered that a body implant having desirable properties can be made from a novel multiple phase polymeric composition having a non-hydrophilic phase and hydrophilic phase, the relative amounts of the non-hydrophilic and hydrophilic components being adjusted, depending on the particular materials employed, to provide a composition having certain properties. The body implant and the composition from which it is made softens and/or swells when in the body and is sufficiently soft when in the body to reduce trauma to the surrounding tissue. Swelling of the implant permits insertion of a smaller device and/or can result in pressure around a wound site reducing bleeding and bacterial invasion into the wound. The implant is sufficiently strong and tough when in the body to maintain its desired shape, to resist deformation and to be capable of removal without tearing and leaving any undesired fragments in the body. For certain applications, the implant has a high initial stiffness for insertion yet softens when in the body to become pliable.

SUMMARY OF THE INVENTION

One aspect of this invention comprises a body implant, at least a portion of which is comprised of a multiple phase polymeric composition comprising:
  (a) a first phase which comprises a substantially non-hydrophilic polymeric component; and
  (b) a second phase which comprises a hydrophilic polymeric component;
said composition (i) being capable of absorbing water to an extent that it softens with a softening ratio of at least about 2:1 and/or swells with a swelling ratio of at least about 1.3:1; and (ii) when substantially completely hydrated, having an energy to break of at least about 700 N-cm/cm$^3$ and a 2.5% Secant modulus of less than about 7,000 N/cm$^2$.

Another aspect of the invention comprises a novel multiple phase composition comprising:

(a) a first phase which comprises a substantially non-hydrophilic polymeric component; and (b) a second phase which comprises a hydrophilic polymeric component;

said composition (i) being capable of absorbing water to an extent that it softens with a softening ratio of at least about 2:1 and/or swells with a swelling ratio of at least about 1.3:1; and (ii) when substantially completely hydrated, having an energy to break of at least about 700 N-cm/cm$^3$ and a 2.5% Secant modulus of less than about 7,000 N/cm$^2$.

A further aspect of the invention comprises a method of making a shaped article comprising:

(1) selecting a mixture comprising a multiple phase polymeric composition comprising:
  (a) a first phase which is continuous and which comprises a substantially non-hydrophilic polymeric component; and
  (b) second phase which comprises a hydrophilic polymeric component;
  said composition (i) being capable of absorbing water to an extent that it softens with a softening ratio of at least about 2:1 and/or swells with a swelling ratio of at least about 1.3:1; and (ii) when substantially completely hydrated, having an energy to break of at least about 700 N-cm/cm$^3$ and a 2.5% Secant modulus of less than about 7,000 N/cm$^2$;

(2) forming the mixture of (1) into a shaped article.

Another aspect of this invention comprises a method of inserting a catheter or cannula into a blood vessel of an animal, said catheter or cannula having a tubular portion and a hub portion, one end of the tubular portion being attached to the hub portion, said method comprising:

(a) selecting a tubular article the walls of which are made of a composition which upon hydration has a softening ratio of at least about 2:1; a swelling ratio of at least about 1.3:1; and a tensile energy to break when substantially completely hydrated of at least about 700 N-cm/cm$^3$;

(b) positioning a portion of the tubular article over a needle such that the inner diameter of the tubing is slightly greater than the outer diameter of the needle, the sharp end of the needle being distal to the hub portion and the attached end of the tubular portion;

(c) inserting the needle into the desired blood vessel of the animal such that both the needle and tubular article are inserted; and (d) retracting the needle leaving a portion of the tubular article in the blood vessel.

Yet another aspect of this invention comprises a method of inserting a catheter or cannula into a blood vessel of an animal, said method comprising:

(a) selecting a tubular article the walls of which are made of a composition which upon hydration has a softening ratio of at least about 2:1; a swelling ratio of at least about 1.3:1; and a tensile energy to break when substantially completely hydrated of at least about 700 N-cm/cm$^3$;

(b) inserting a needle having an inner diameter slightly larger than the outer diameter of the tubular article into the desired blood vessel;

(c) positioning a portion of the tubular article through the needle and then into the blood vessel for a predetermined distance; and (d) retracting the needle leaving a portion of the tubular article in the blood vessel.

DETAILED DESCRIPTION OF THE INVENTION

Figure 1:
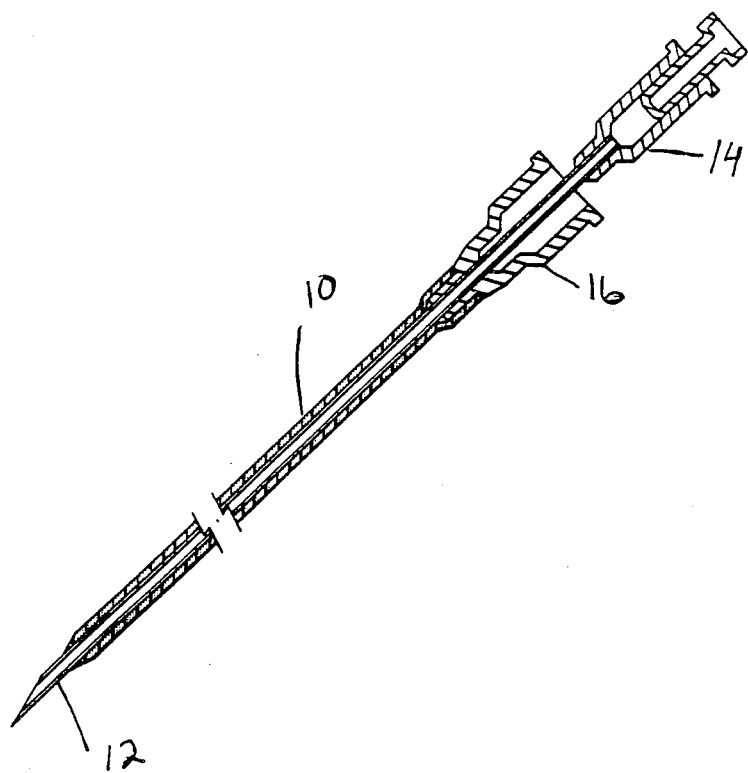
FIG. 1 is a side elevation view of an IV catheter or cannula of this invention arranged over a needle for insertion into a blood vessel of an animal.

The body implant of this invention comprises a multiple phase polymeric composition comprising a first phase which comprises a substantially non-hydrophilic polymeric component and a second phase which comprises a hydrophilic polymeric component. The relative amounts of these components are selected, depending on the particular polymeric materials employed, to provide a composition having the desired properties, as discussed more fully below.

Preferably the non-hydrophilic polymeric component forms a continuous phase. The hydrophilic polymeric component can form a co-continuous phase with, or a dispersed phase in, the non-hydrophilic polymer phase.

The non-hydrophilic polymeric component comprises a polymer which does not substantially absorb or attract water. Preferably, the non-hydrophilic polymer is capable of absorbing water in an amount of no more than about 30%, more preferably no more than about 15%, and most preferably no more than about 10%, by weight, based on the weight of the non-hydrophilic polymer.

The non-hydrophilic polymer can be for example, a polyurethane such as an aliphatic polyurethane, a polyether polyurethane, a polyester polyurethane; and ethylene copolymer such as ethylene-vinyl acetate copolymer or ethyleneethyl acrylate copolymer; a polyamide, in particular a polyamide of low crystallinity; aliphatic polyesters; or the like. A particularly preferred non-hydrophilic polymer is a polyurethane, especially an aliphatic polyurethane.

The hydrophilic polymer preferably is a polymer that absorbs at least about 50% water, more preferably about 100%, for example, at least about 150%, by weight based on the weight of the hydrophilic polymer. The hydrophilic polymer preferably forms a hydrogel on absorption of water.

The hydrophilic polymer is preferably polyvinyl alcohol, poly(ethylene oxide), polypropylene oxide, poly(ethylene glycol) polypropylene glycol, polytetramethylene oxide, polyvinyl pyrolidene, polyacrylamide, poly(hydroxy ethyl acrylate), poly(hydroxyethyl methacrylate), or the like.

The multiple phase composition can be prepared by mixing the polymeric components or by forming a block or graft copolymer containing the polymeric components. A mixture of the components can be prepared using, for example, a two-roll mill, an internal mixer, such as a Brabender or Banbury mixer, and extruder, e.g. twin-screw extruder, or the like. Block and graft copolymers can be prepared by appropriate methods depending on the particular nature of the components used. Typical preparatory methods can be found, for example, in "Block and Graft Copolymerization", R. J. Ceresa (Zd), 1973, Vol. 1 & 2, Wiley-Interscience, New York and "Block Copolymers", D. C. Allport and W. H. Jane, 1973, Wiley, New York.

Generally, the ratio of non-hydrophilic polymeric component to hydrophilic polymeric component is 0.65:1 to 9:1. Preferably the ratio of the polymeric component is 1:1 to 9:1.

The polymeric components are selected to provide a multiple phase system. Generally, the polymeric components each have a molecular weight of at least about 3,000 preferably at least about 5,000 and most preferably at least about 10,000.

As stated above, the relative amounts of non-hydrophilic and hydrophilic polymeric components are selected, depending on the particular materials employed, to provide the desired properties. Due to the presence of the hydrophilic polymeric component, the composition is capable of being hydrated by the absorption of water. As water is absorbed by the composition, it may soften with a softening ratio of at least about 2:1, preferably at least 6:1, more preferably at least about 10:1, most preferably at least about 20:1, and in particular at least about 40:1. The term "softening ratio" is used herein to refer to the ratio of the 2.5% Secant modulus values of the composition, in the form of a tubular article, when substantially non-hydrated, to the 2.5% Secant modulus of the composition when substantially completely hydrated. The term "substantially non-hydrated" refers to the state of the composition under conventional ambient conditions, i.e. room temperature, 50–80% relative humidity and about atmospheric pressure. The term "substantially completely hydrated" refers to the state of the composition when it is in equilibrium with an excess of water at 37° C. and ambient pressure.

The composition may swell on absorption of water with a swelling ratio of at least about 1.3:1, preferably at least about 1.7:1 and most preferably at least about 2.0:1. The term "swelling ratio" refers to the ratio of the volume of a given sample of the composition when substantially completely hydrated to its volume when substantially non-hydrated.

Preferably the composition both softens and swells when placed in the body.

When substantially completely hydrated the composition has a tensile energy to break of at least about 700 Newton-centimeters per cubic centimeter (N-cm/cm$^3$), preferably at least about 1,400 N-cm/cm$^3$ and most preferably about 1,700 N-cm/cm$^3$. The term "tensile energy to break" (TEB) is defined in ASTM-D882 as the area under the stress-strain curve or $$TEB = \int_0^{\epsilon_T} S d\epsilon$$

where S is the stress at any strain, $\epsilon_i$; and $\epsilon_T$ is the strain at rupture. The tensile energy to break provides an indication of the toughness of the hydrated composition and its ability to withstand the conditions it will be subjected to in use.

It will be readily appreciated that when a tubular product such as a catheter or cannula is withdrawn from the body it is extremely important that it does not tear or break leaving pieces remaining inside the body. Neither tensile strength nor elongation to break are good indicators of toughness. Brittle materials and notch sensitive materials can have high tensile strengths. Extremely weak materials can have high elongation but not the strength to survive extraction. TEB is a measure of the energy required to break and is a combination of these two important criteria.

The ultimate elongation of the multiple phase composition should be at least about 10%, preferably at least about 25% and most preferably at least about 50%.

The composition when substantially completely hydrated has a 2.5% Secant modulus of less than about 7,000 Newtons/square centimeter (N/cm$^2$), preferably less than about 3,500 N/cm$^2$ and most preferably less than about 2,000 N/cm$^2$. When substantially completely hydrated the 2.5% Secant modulus can be as low as about 30 N/cm$^2$ but preferably above about 60 N/cm$^2$ and most preferably above about 120 N/cm$^2$.

Typically the 2.5% Secant modulus of the composition when substantially non-hydrated is at least about 20,000 N/cm$^2$ when used as an over the needle catheter as described more fully below. Preferably the 2.5% Secant modulus of the composition is at least about 28,000 N/cm$^2$ for this particular use. For other proposed uses of the composition a lower modulus may be desirable. For example, for use as a catheter in a through the needle device, as described more fully below, the 2.5% Secant modulus of the composition can be in the range of about 7,000 to about 20,000 N/cm$^2$ The composition may be crosslinked if desired. Crosslinking of the composition gives the polymeric composition strength above the melting or softening points of the polymeric components permitting sterilization of a device utilizing the composition at above that temperature. This is particularly advantageous if the polymeric component of continuous phase has a relatively low melting or softening point. Crosslinking of the composition may also be used to adjust the 2.5% Secant modulus of the composition to bring it to the desired value for the proposed use of the composition. When the composition comprises a physical mixture of the non-hydrophilic and hydrophilic components, crosslinking of the mixture can control the tendency of the hydrophilic component to leach out of the composition when it is in extended contact with water or body fluids. Crosslinking may also improve the toughness (TEB) of the composition in the hydrated state.

Crosslinking of the composition can be effected by use of an appropriate crosslinking agent or by irradiation, preferably in the presence of a crosslinking promoter, such as triallyl isocyanurate, or the like. In a preferred embodiment the composition is crosslinked by high energy radiation from an electron accelerator. The amount of irradiation should be in the range of about 0.5 to about 30 Megarads (Mrads) preferably about 0.5 to about 15 Mrads and most preferably about 0.5 to about 10 Mrads.

Either or both components of the composition may contain additional ingredients such as stabilizers, antioxidants, radiopacifiers, medicaments, fillers or the like. For certain applications it may be advantageous to incorporate a water soluble or water dispersible medicament which can leach from the composition of the implant when it contacts body fluids. Such medicaments include anti-thrombogenic agents, antibiotics, anti-viral agents, anticoagulants, anti-inflammatory agents or the like.

As mentioned above the compositions of this invention are particularly useful for making articles suitable for use as body implants. The body implant can take any desired shape such as a film, rod, filament, tube or the like. The composition can be formed into a shaped article and can be crosslinked, if desired, before or after the shaping step.

In particular the compositions of this invention are useful for making catheters for use in intravenous (IV) devices. Tubular articles of this invention can be used in both over the needle and through the needle techniques of introducing an IV device into the blood vessel of an animal. The term animal is used to refer to any member of the animal kingdom which may be treated using an IV technique and in particular refers to mammals such as horses, cattle, dogs, cats and humans.

The use of a catheter of this invention in an over the needle technique for administering a fluid intravenously is illustrated in FIG. 1. In FIG. 1 catheter, 10, of this invention fits snugly over a needle, 12, and at the distal end, the catheter wall is tapered to a feathered edge. Both the needle and the catheter have a female luer fitting, 14 and 16, respectively, at the proximal end. The needle/catheter assembly is advanced through the skin and into the blood vessel (vein). The needle is then withdrawn leaving the catheter in place. An IV line is connected to the catheter by means of the luer fitting.

The tubular article used as the catheter in this application is of a composition which softens and swells as defined above. The 2.5% Secant modulus of the catheter prior to insertion should be at least about 20,000 N/cm$^2$, it should soften with a softening ratio of at least about 2:1, should swell with a swelling ratio of at least about 1.3:1 and should achieve a 2.5% Secant modulus after being in contact with the blood of the vein of less than about 7,000 N/cm$^2$. The catheter should retain its hardness during its insertion. The catheter should not swell or soften appreciably during the time it is being inserted. It has been found that the time for the catheter to swell 50% of its fully swollen volume should be at least about 15 seconds, preferably at least about 60 seconds.

Figure 2:
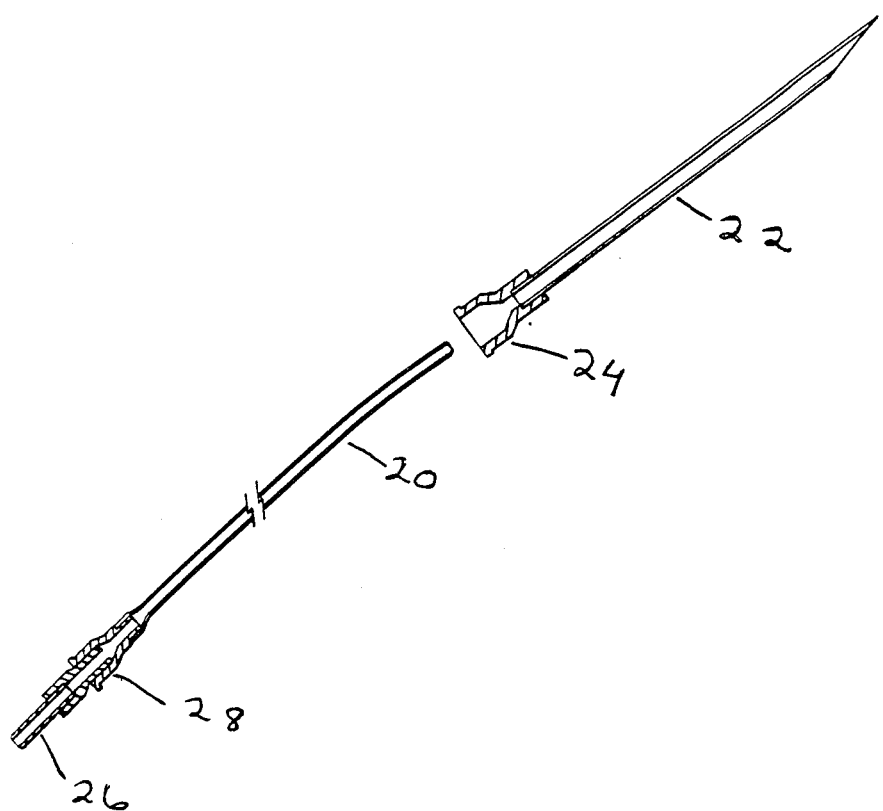
FIG. 2 is a side elevation view of an IV catheter or cannula of this invention and a hollow needle through which the catheter or cannula can be inserted after the needle has been inserted in a blood vessel of an animal.

Another insertion technique is the through the needle technique and is illustrated in FIG. 2. With this insertion technique, the venipuncture is made using either a conventional needle, 22, fitted with luer fitting, 24. After the vein entry, a catheter, 20, that is preconnected to an IV line, 26 through luer fitting 28, is threaded through the needle 22 into the vein (not shown). In this technique, a catheter which swells to 50% of its fully swollen volume in not less than 30 seconds, preferably in not less than 60 seconds, is preferably used. Once the catheter is in place, the needle is retracted. If a conventional needle is used, it is left on the catheter and placed in a protective plastic sheath. If a break-away needle is used, the needle is split into two along its axis and discarded.

Because the catheters of this invention become relatively soft after insertion, they tend to cause less irritation to the intima (lining of the vein) and to the insertion site and, therefore, are less likely to contribute to mechanical phlebitis. The catheters may contain a slow release medicament. The softness of the catheter permits it to float in the vein rather than lie on the point where inserted and consequently the medication is delivered evenly helping to avert chemical phlebitis.

Because these catheters swell, the gauge size of the catheter used can be smaller than that of a non-swelling catheter for a given flow requirement. This allows access to smaller veins in the limb extremities and easier insertion into the vein. In addition, the swelling of the catheter seals the wound site more effectively and helps prevent catheter slip out, a common cause for changing catheters prematurely.

The following examples illustrate typical compositions of this invention and their uses in preparing shaped articles useful as body implants.

EXAMPLES 1 TO 7

BLENDS

For each Example, the ingredients and the amounts thereof, in parts by weight, indicated in the Table I, were mixed together on a heated (150°–160° C.) mill, about 20–30% of the polyurethane being added first, then about 30% of the polymer capable of forming a hydrogel then about 20–30% of the polyurethane, then the remainder of the polymer capable of forming a hydrogel and finally the remainder of the polyurethane. The mixture was stripped from the mill and pressed into slabs 6"×6" and about 25 mils thick. The slabs were tested after they had been irradiated (i.e. exposed to electrons in a radiation beam) to a dose of 10 Mrad. The secant modulus for the dry state was measured by the procedure of ASTM D-882. Each sample was immersed in water at body temperature (37° C.) for between 10 minutes and 3 hours to hydrate the blend. The hydrated secant modulus was then determined by the same procedure. The softening ratio was calculated.

In the Table I below, the polymers are identified by their trade names; they have either been described already, in the earlier part of this specification, or are further described below.

TABLE I

| Example Formulations | PARTS BY WEIGHT | | | | | | |
|---|---|---|---|---|---|---|---|
| | 1 | 2 | 3 | 4 | 5 | 6 | 7 |
| Polyvinyl Alcohol | 20 | — | — | — | — | — | — |
| Polyethylene Glycol 8000 | — | 20 | — | — | 30 | — | — |
| Polyethylene Oxide WSR-301 | — | — | — | — | — | 30 | — |
| Polyethylene Oxide WSR-3154 | — | — | 10 | 20 | — | — | 30 |
| Polyurethane 70D (Tecoflex) | — | — | — | 80 | — | — | — |
| Polyurethane 60D (Tecoflex) | 80 | 80 | 90 | — | 70 | 70 | 70 |
| Beamed Data | | | | | | | |
| Dry Secant Modulus N/cm$^2$ | 6,320 | 4,280 | 2,695 | 10,558 | 4,387 | 3,734 | 3,576 |
| Wet Secant Modulus N/cm$^2$ | 1,788 | 1,305 | 1,210 | 3,709 | 1,055 | 1,738 | 147 |
| Softening Ratio | 3.5 | 3.27 | 2.23 | 2.85 | 4.16 | 2.15 | 24.4 |

EXAMPLE 8

Cannula Tubing

A blend of 3 grams of Sartomer 295, 138 grams of Tecoflex 60D, and 59 grams of Polyox WSR3154 (Example 7) was compounded in 200 gram batches on the mill as described earlier. The blend was chopped on a Nelmor chopper; the tubing was extruded on a Wayne ¾" extruder; and irradiated at 10 Mrads.

The irradiated tubing, having an initial I.D. of 0.91 mm and an O.D. of 1.27 mm, experienced a swell of 0.101 mm in the I.D. and 0.254 mm in the O.D. for a 0.076 mm wall thickness swell (43%) by uptake of water during immersion in Ringer's solution.

Tubing samples were conditioned for 1 hour at 37° C. in Ringers's Solution to provide specimens in the hydrated state. Ringer's Solution is a sterile solution for parenteral administration containing 147 milliequivalents (meq) Na+ per liter, 4 meq K+/1, 4 meq Ca+2/1 and 155 meq Cl-/1. The solution closely simulates body fluid electrolytes.

The volume swell ratio and dry and hydrated 2% Secant Moduli are reported in the following table.

| Volume Swell Ratio | Hydrated Secant Modulus | Dry Secant Modulus |
|---|---|---|
| >1.66:1 | 1,724 N/cm² | 20,684 N/cm² |

EXAMPLE 9

Four blends were compounded in 200 gram batches on the mill as described earlier. These blends were then chopped on a Nelmor chopper; then extruded into tubing on a ¾" Wayne crosshead extruder; and then irradiated with a 10 Megarad dosage.

The formulations (% weight) were:

| Sample | 1 | 2 | 3 | 4 |
|---|---|---|---|---|
| Polyethylene Oxide (Union Carbide WSR301) | 29.1 | 23.7 | 29.1 | 34.0 |
| Polyurethane (Thermidics EG-60D) | — | — | — | 63.1 |
| Polyurethane with 20% Barium Sulfate (Thermedics EG-60D-20B) | 68.0 | — | — | — |
| Polyurethane with 40% Barium Sulfate (Thermedics EG-60D-40B) | — | 73.4 | — | — |
| Polyurethane with 20% Bismuth Subcarbonate (Thermedics EG-60D-20HC) | — | — | 68.0 | — |
| Titanium Dioxide (Tipure R101) | 1.5 | 1.5 | 1.5 | 1.5 |
| Butylated Hydroxy Toluene | .3 | .3 | .3 | .3 |
| Butylated Hydroxy Anisole | .3 | .3 | .3 | .3 |
| Pentaerythritol Tetraacrylate | .8 | .8 | .8 | .8 |
| | 100.0 | 100.0 | 100.0 | 100.0 |

The irradiated tubing, having an I.D. of approximately 1.04 mm and an O.D. of approximately 1.40 mm was tested for tensile properties, energy to break and swell both in the dry state and after 24 hour immersion in 37° C. distilled water.

The following results are for these four samples (1–4) and samples of commonly used medical catheter materials when submitted to the same test procedure.

| | Dry 23° C. 2.5 Secant Modulus N/cm² | Hydrated 37° C. 2.5% Secant Modulus N/cm² | Volume Swell Ratio | Softening Ratio | Energy N—cm/cm³ |
|---|---|---|---|---|---|
| Sample 1 | 31,033 | 282 | >2.0:1 | 110:1 | 3,144 |
| 2 | 22,960 | 296 | >1.9:1 | 77:1 | 3,492 |
| 3 | 23,196 | 387 | >1.7:1 | 60:1 | 3,098 |
| 4 | 20,688 | 323 | >1.9:1 | 64:1 | 4,471 |
| FEP Catheter mat'l # A | 34,681 | 26,967 | 1:1 | 1.3:1 | 9,782 |
| FEP Catheter mat'l # B | 40,113 | 35,317 | 1:1 | 1.1:1 | 13,035 |

We claim:

1. An article, suitable for use as a body implant, having been formed from a multiple phase polymeric composition comprising:
   (a) a first phase which is continuous and comprises a substantially non-hydrophilic polymeric component capable of absorbing water in an amount of no more than about 30% by weight based on the weight of the non-hydrophilic polymer; and
   (b) a second phase which comprises a hydrophilic polymeric component capable of absorbing at least about 50% water, by weight based on the weight of the hydrophilic polymer;
   wherein said article (i) is capable of absorbing water to an extent that it softens with a softening ratio of at least about 2:1 or swells with a swelling ratio of at least about 1.3:1; and (ii) has an energy to break of at least about 700 N-cm/cm³ and a 2.5% Secant modulus of less than about 7,000 N/cm², when substantially completely hydrated.

2. An article in accordance with claim 1, wherein said second phase is dispersed in said continuous first phase.

3. An article in accordance with claim 1, wherein said non-hydrophilic polymer component comprises a polyurethane an ethylene-vinyl acetate copolymer, an ethylene-ethyl acrylate copolymer, a low crystalline polyamide or an aliphatic polyester.

4. An article in accordance with claim 3, wherein the non-hydrophilic polymer component comprises a polyurethane.

5. An article in accordance with claim 1, wherein the hydrophilic polymeric component comprises polyvinyl alcohol, poly(ethylene oxide), polypropylene oxide, poly(ethylene glycol), polypropylene glycol, polytetramethylene oxide polyvinyl propylidene, polyacrylamide, poly(hydroxy ethyl acrylate) or poly(hydroxyethyl methacrylate).

6. An article in accordance with claim 5, wherein the hydrophilic polymeric component comprises poly(ethylene oxide).

7. An article in accordance with claim 1, wherein said multiple phase composition comprises a physical mixture of said polymeric components.

8. An article in accordance with claim 1, wherein said composition position is crosslinked.

9. An article in accordance with claim 1, wherein the composition position has a softening ratio of at least about 6:1.

10. An article in accordance with claim 1, wherein the composition position has a softening ratio of at least about 10:1.

11. An article in accordance with claim 1, wherein the composition has a swelling ratio of at least about 1.7:1.

12. An article in accordance with claim 1, wherein the composition has a swelling ratio of at least about 2.0:1.

13. An article in accordance with claim 1, wherein the composition has a energy to break of at least about 1400 N-cm/cm$^3$.

14. An article in accordance with claim 1, wherein the composition has a 2.5% Secant modulus when hydrated of less than about 4,000 N/cm$^2$.

15. An article in accordance with claim 1, which is a tubular article, the walls of which are made of said composition.

16. An article in accordance with claim 15, which is a catheter or cannula.

17. An tubular article suitable for use as a catheter or cannula the walls of which have been formed from a multiple phase polymeric composition comprising a physical mixture of:
  (a) a first phase which is continuous and comprises a substantially non-hydrophilic polymeric component capable of absorbing water in an amount of no more than about 30% by weight based on the weight of the non-hydrophilic polymer; and
  (b) a second phase which comprises a hydrophilic polymeric component capable of absorbing at least about 50% water, by weight based on the weight of the hydrophilic polymer;
wherein said article (i) is capable of absorbing water to an extent that it softens with a softening ratio of at least about 2:1 a swelling ratio of at least about 1.3:1; and (ii) has an energy to break of at least about 700 N-cm/cm$^3$ and a 2.5% Secant modulus of less than about 7,000 N/cm$^2$, when substantially completely hydrated.

18. A tubular article in accordance with claim 17, wherein said non-hydrophilic polymeric component comprises a polyurethane.

19. A tubular article in accordance with claim 17, wherein said hydrophilic component comprises polyethylene oxide.

20. An article suitable for use as a body implant, having been formed from a multiple phase polymeric composition comprising:
  (a) a first phase which is continuous and comprises a substantially non-hydrophilic polyurethane; and
  (b) a second phase which comprises a hydrophilic polyethylene oxide;
wherein said article (i) is capable of absorbing water to an extent that it softens with a softening ratio of at least about 2:1 or swells with a swelling ratio of at least about 1.3:1; and (ii) has an energy to break of at least about 700 N-cm/cm$^3$ and a 2.5% Secant modulus of less than about 7,000 N/cm$^2$, when substantially completely hydrated.

21. An article in accordance with claim 20, wherein said second phase is dispersed in said continuous first phase.

22. An article in accordance with claim 21, wherein said multiple phase composition comprises a physical mixture of said polymeric components.

23. An article in accordance with claim 22, wherein said composition is crosslinked.

24. An article in accordance with claim 20, wherein the composition has a softening ratio of at least about 6:1.

25. An article in accordance with claim 20, wherein the composition has a softening ratio of at least about 10:1.

26. An article in accordance with claim 20, wherein the composition has a swelling ratio of at least about 1.7:1.

27. An article in accordance with claim 20, wherein the composition has a swelling ratio of at least about 2.0:1.

28. An article in accordance with claim 20, wherein the composition has a energy to break of at least about 1400 N-cm/cm$^3$.

29. An article in accordance with claim 20, wherein the composition has a 2.5% Secant modulus when hydrated of less than about 4,000 N/cm$^2$.

30. A tubular article suitable for use as a catheter or cannular the walls of which have been formed from a multiple phase polymeric composition comprising a physical mixture of:
  (a) a first phase which is continuous and comprises a substantially non-hydrophilic polyurethane; and
  (b) a second phase which comprises a hydrophilic polyethylene oxide;
wherein said article (i) is capable of absorbing water to an extent that it softens with a softening ratio of at least about 2:1 or swells with a swelling ratio of at least about 1.3:1; and (ii) has an energy to break of at least about 700 n-cm/cm$^3$ and a 2.5% Secant modulus of less than about 7,000 N/cm$^2$, when substantially completely hydrated.

* * * * *